(12) United States Patent
Proglhof

(10) Patent No.: US 6,428,523 B1
(45) Date of Patent: Aug. 6, 2002

(54) SANITARY NAPKIN

(75) Inventor: Igor Philip Passos Proglhof, Sao Paulo (BR)

(73) Assignee: Johnson & Johnson Industria E Comercio LTDA (BR)

(*) Notice: Subject to any disclaimer, the term of this patent is extended or adjusted under 35 U.S.C. 154(b) by 0 days.

(21) Appl. No.: 09/651,363

(22) Filed: Aug. 30, 2000

(51) Int. Cl.$^7$ ................................................. A61F 13/15
(52) U.S. Cl. ........................... 604/385.04; 604/385.03; 604/386; 604/387
(58) Field of Search ................ 604/385.03, 385.04, 604/386, 387, 389, 385.05

(56) References Cited

U.S. PATENT DOCUMENTS

| | | | |
|---|---|---|---|
| 4,917,697 A | | 4/1990 | Osbornm, III et al. |
| 4,940,462 A | | 7/1990 | Salerno |
| 5,591,147 A | * | 1/1997 | Couture-Dorschner et al. .. 604/369 |
| 5,626,572 A | * | 5/1997 | Ahr et al. ................. 604/385.1 |
| 5,650,223 A | * | 7/1997 | Weinberger et al. .......... 442/62 |
| 5,681,303 A | * | 10/1997 | Mills et al. .............. 604/385.2 |
| 5,704,928 A | | 1/1998 | Morita |

FOREIGN PATENT DOCUMENTS

| | | |
|---|---|---|
| WO | 93/06805 | 4/1993 |
| WO | 95/03022 | 2/1995 |
| WO | 96/10977 | 4/1996 |
| WO | 96/14816 | 5/1996 |
| WO | 97/12576 | 3/1997 |

* cited by examiner

*Primary Examiner*—John G. Weiss
*Assistant Examiner*—Jacqueline F Stephens

(57) ABSTRACT

A sanitary napkin provided with wings, and particularly a women's sanitary napkin. There is disclosed a sanitary napkin provided with wings that are adapted to be folded over the edges of an undergarment and tension relief structures which are located on a garment faceable surface of the wings. The tension relief structures have first surface affixed to a garment faceable surface of the wing and a second surface that is adapted to contact the undergarment in use. The second surface is movable with respect to the first surface and the second surface has an adhesive region that releasably adheres the tension relief structure to the user's undergarment.

9 Claims, 3 Drawing Sheets

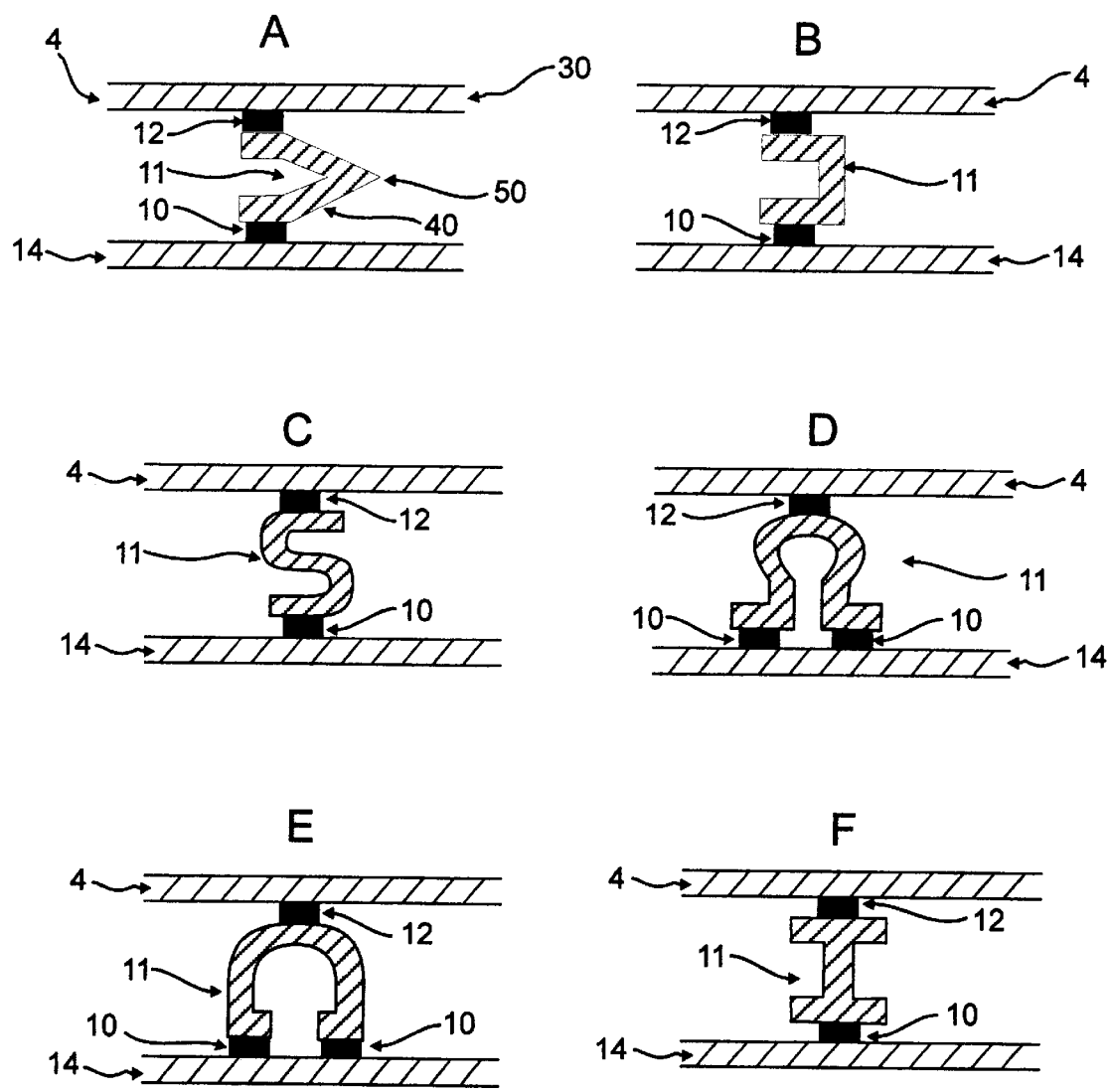

SANITARY NAPKIN

DISCLOSURE OF THE INVENTION

The present invention relates to a sanitary napkin provided with wings and more particularly to a women's sanitary napkin provided with wings having a tension relief means.

DESCRIPTION OF THE STATE OF THE ART

As known in the art, women's sanitary napkins are generally disposable and used to collect and contain vaginal exudates, especially menstrual blood and intermenstrual secretions.

Such napkins are usually comprised of a substantially flat oblong absorbing core wrapped by a top layer and a lining layer. The top layer contacts the pelvic region of the user and is usually made of permeable material that does not cause any irritation to the skin. The purpose of the lining layer, which is generally made of impervious material and opposite the top layer, is to prevent the collected fluid retained in the napkin core from touching the user's clothes.

The attachment of the sanitary napkin to the lingerie is generally attained through adhering regions in the lining layer that are stuck to the user's undergarment.

The materials of the top layer, lining layer, napkin core, and the types of adhesive are fully known by one skilled in the art.

Currently, a great number of women's sanitary napkins are provided with flexible wings that extend laterally from the sides of the napkin core and are adapted to be folded over a crotch portion of the wearer's undergarment. The wings may be formed as a prolongation of one or both said lining and top layers, or alternatively, may be formed from separate layers which are affixed to the napkin. Said wings perform at least two functions: they fix said napkin to the user's undergarment, thus preventing same from displacing therefrom, and prevent the exudates from leaking through the sides of the napkin. Those two functions contribute to a reduction in the occurrence of stains in the user's clothes.

During the use of a napkin provided with side wings, the latter are folded around the edges of the portion of the undergarment to be lodged between the user's thighs, being attached to the external face thereof. Preferably, one or more surfaces of said wings have adhesive coated regions, thus promoting the attachment to the external face of the undergarment and preventing the napkin from being displaced while in use.

While napkins provided with side wings are normally seen as more efficient than the ones without side wings for the attachment to undergarment, there still exist problems with current wing designs. Foe example, occasionally the wings become unattached from the undergarment due to the stresses to which they are submitted while in use. As the wings are folded over the edges of the undergarment while in use, stresses occur which are especially high along the folding line which is curved since it runs along the edges of the crotch portion of the undergarment to be lodged between the user's thighs. Such stresses increase as the user moves, for example, by walking or crossing her legs, at which time the edges of the undergarment are pulled against the wings of the napkin, thus increasing-the stress against the folding line. The stress increases to a level wherein the wing becomes unattached from the undergarment, thus eliminating the advantages attained by this way of attaching the napkin thereto.

Despite the difficulty in assuring the absolute integrity of a napkin, as well as its fixation at a certain position, in view of the anatomy of the user and her movements, the conception of napkins that at least reduce the above-mentioned problems has been a constant worry.

The technique prior to the present invention is prodigal in expedients for solving such problems, some of which were described in documents WO 93/06805, WO 95/03022, WO 96/14816, WO 96/10977, WO 97/12576, U.S. Pat. No. 4,917,697 and U.S. Pat. No. 4,940,462.

Such documents suggest modifying the traditional wings such as by changing their surface thus allowing same to extend more, including undercuts and folds, or providing multiple overlapped elements. The purpose of all these disclosures is to have the wing itself as the tension relief means. However, this makes the structure of the wing more complex, more expensive, or more inconvenient to the user.

BRIEF DESCRIPTION AND OBJECTS OF THE INVENTION

An object of the present invention is to provide a sanitary napkin provided with wings which is simple and efficient in preventing the wings from becoming unattached from the undergarment when in use.

Another object of the present invention is to provide a sanitary napkin provided with wings and tension relief structures which are not located in the respective wing folding zones, but rather in the focal points of undesirable stresses, that is, the points where said wings are attached to the external face of the undergarment, generally by means of an adhesive.

Still one another object of the present invention is a sanitary napkin provided with wings and a tension relief structure which is similar to the traditional product the user is familiar to and does not require special manipulation, different from the one currently used.

Such objects are attained by a sanitary napkin provided with side wings wherein at least one of said wings is provided with a tension relief structure, thus associating, during the use, said wing with the user's undergarment.

In accordance with the present invention, there has been provided a sanitary napkin comprising a body faceable liquid permeable top layer, a garment faceable liquid impermeable lining layer and an absorbing core intermediate the top layer and the lining layer, the sanitary napkin further including a flexible wing adapted to be folded over a crotch portion of a wearer's undergarment in use, wherein said wing is provided with a tension relief structure, the tension relief structure having first surface affixed to a garment faceable surface of the wing and a second surface that is adapted to contact the undergarment in use, the second surface being movable with respect to the first surface and the second surface having an adhesive region that releasably adheres the tension relief structure to the user's undergarment.

As used in this context, the terminology "a tension relief structure" means a physical arrangement, for example, a flexible form provided with a certain volume which is not integral with the continuous surface of the wing itself The present invention is not intended to include wing structures wherein tension relief is provided by replacing the conventional material within the wing with a material this is capable of being stretched and distorted when submitted to stresses, nor does it include cuts or slits in the wings, or changes in the profile thereof such as by ring rolling or similar techniques.

Preferably, the tension relief structure is permanently adhered to the surface of the wing in such a way that, during the use of the absorbing article, it folds and turns onto the external face of the region of the undergarment to be lodged between the user's thighs. And the tension relief structure associates the wing with the user's undergarment, thus preferably providing a non-permanent adhesion between them, for example, by a pressure sensitive adhesive usually known as PSA.

Typical examples of the tension relief structure are hollow or non-hollow spatial arrangements provided or not with continuous surfaces made of flexible and/or elastic material, for example, in the shape of a pipe, a sphere, an angle-iron, a joint, a handle, a polyhedron, a block of foam, sponge or rubber, etc. A basic feature of the tension relief structure in accordance with the invention is that two distinct lengths of its surface, when adhered to two bodies that move independently, are able to follow such movements by distorting in such a way to prevent the association between the two bodies from being disrupted.

In other words: usually two surfaces adhered to each other (in this case the surface of the undergarment and the wing-shaped surface of a sanitary napkin), when submitted to shear forces, tend to separate when one of them slides over the other in opposite directions, until the applied force overcomes the deformation capacity of the adhesive layer and said surfaces separate from each other. When according to the invention a deformable, extensible and/or elastic structure that can suffer a certain deformation without losing the adhesion thereto is inserted between said surfaces, its capacity to keep the two surfaces joined together is increased.

BRIEF DESCRIPTION OF THE DRAWING

The present invention will be described in details below based on a practical example represented in the accompanying figures, wherein.

DETAILED DESCRIPTION OF THE FIGURES

Figure 1:
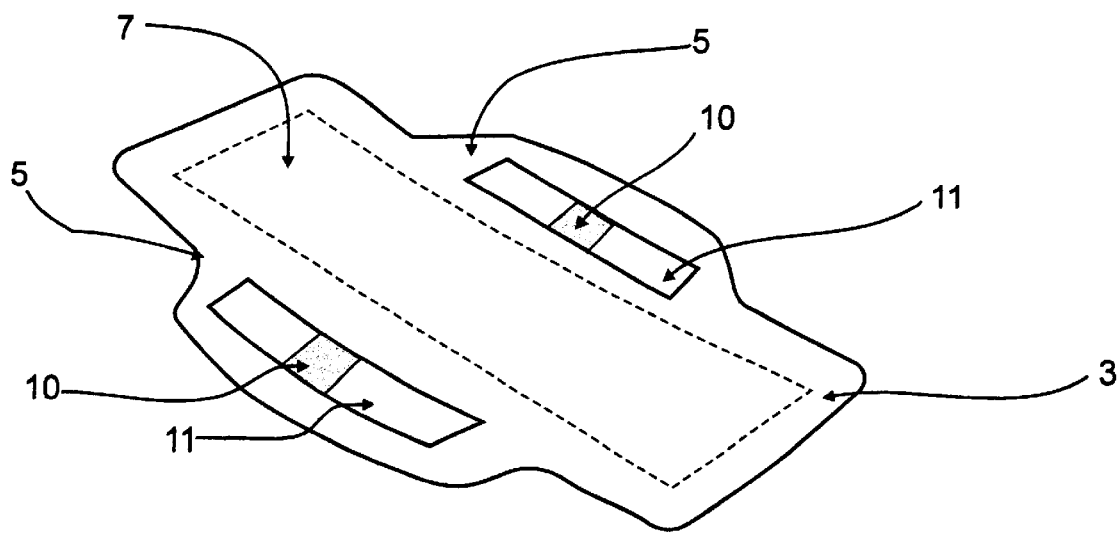
FIG. 1 is a perspective view of a preferred embodiment of the sanitary napkin made in accordance with the present invention.
Figure 2:
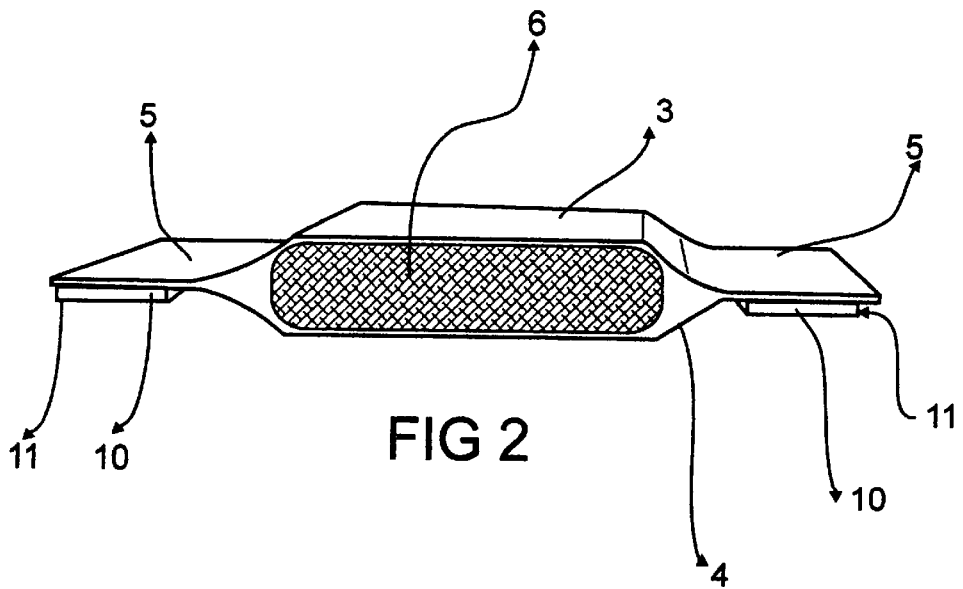
FIG. 2 is a perspective cross-sectional view of a transverse cut of the napkin shown in FIG. 1.

With reference to FIGS. 1 and 2, it can be seen that the sanitary napkin of the present invention is comprised of a longitudinally oblong absorbing core 6 wrapped by a top layer 3 and a lining layer 4. The top layer 3 is intended to contact the pelvic region of the user, and the purpose of the lining layer 4, opposite the top layer, is to prevent the collected fluid retained in the napkin core 6 from touching the user's clothes when in use. The napkin 1 of the example is also comprised of a longitudinal central adhering region 7 applied onto the lining layer 4 to releasably attach the napkin 1 to the user's undergarment. Said region 7 can be optionally omitted.

The napkin 1 is also comprised of flexible wings 5 that extended laterally, in this example as a prolongation of both said top layer 3 and lining layer 4, but can be a prolongation of only one of them, or also be structurally distinct from said layers 3 and 4 but affixed to the side of the napkin 1. The wings 5 (or at least one of them) are provided with tension relief structures 11 having a first side attached to the wing and a second side opposite the first side, the second side having an adhesive coated region 10 on a garment faceable surface of the second side. The first side is movable with respect to the second side so that the wing 5 will be capable of a certain degree of displacement after the wing 5 has been attached to the user's undergarment, as a function of the side movement provided by the tension relief structure 11. The adhesive coated regions 10 may have any shape and may be formed by points, lines or bands of adhesive. Preferably, the adhesive coated regions 10 have a generally square or rectangular shape.

In accordance with a preferred embodiment, said tension relief structure 11 is in the shape of a cylindrical pipe attached to a respective wing 5 which is parallel to said axis. When the adhesive coated region 10 is provided in the structure 11 on a side opposite the one to be attached to the wing 5, it can be seen that the napkin 1 will show a certain displacement degree after its wings 5 have been attached to the user's undergarment, as a function of the side movement provided by the tension relief structure 11.

Said movement substantially refrains or prevents the wings 5 from becoming unattached from the external surface of the region of the undergarment to be lodged between the user's thighs. The same effect occurs if one of the wings 5 is adhered over the other.

Of course the extension of said movement will vary as a function of the diameter of the structure 11—a cylinder, in this embodiment—and as a function of the width of the adhesive coated region 10. The extent of said extension can also be increased if the structure 11 is made of corrugated and/or elastic material.

As already indicated, the tension relief structure 11 is optionally hollow, but can have other shapes in addition to the cylindrical one, such as spherical, in which case it can advantageously be attached to the respective wing 5 only at a point opposite the adhesive coated region 10.

Figure 3:
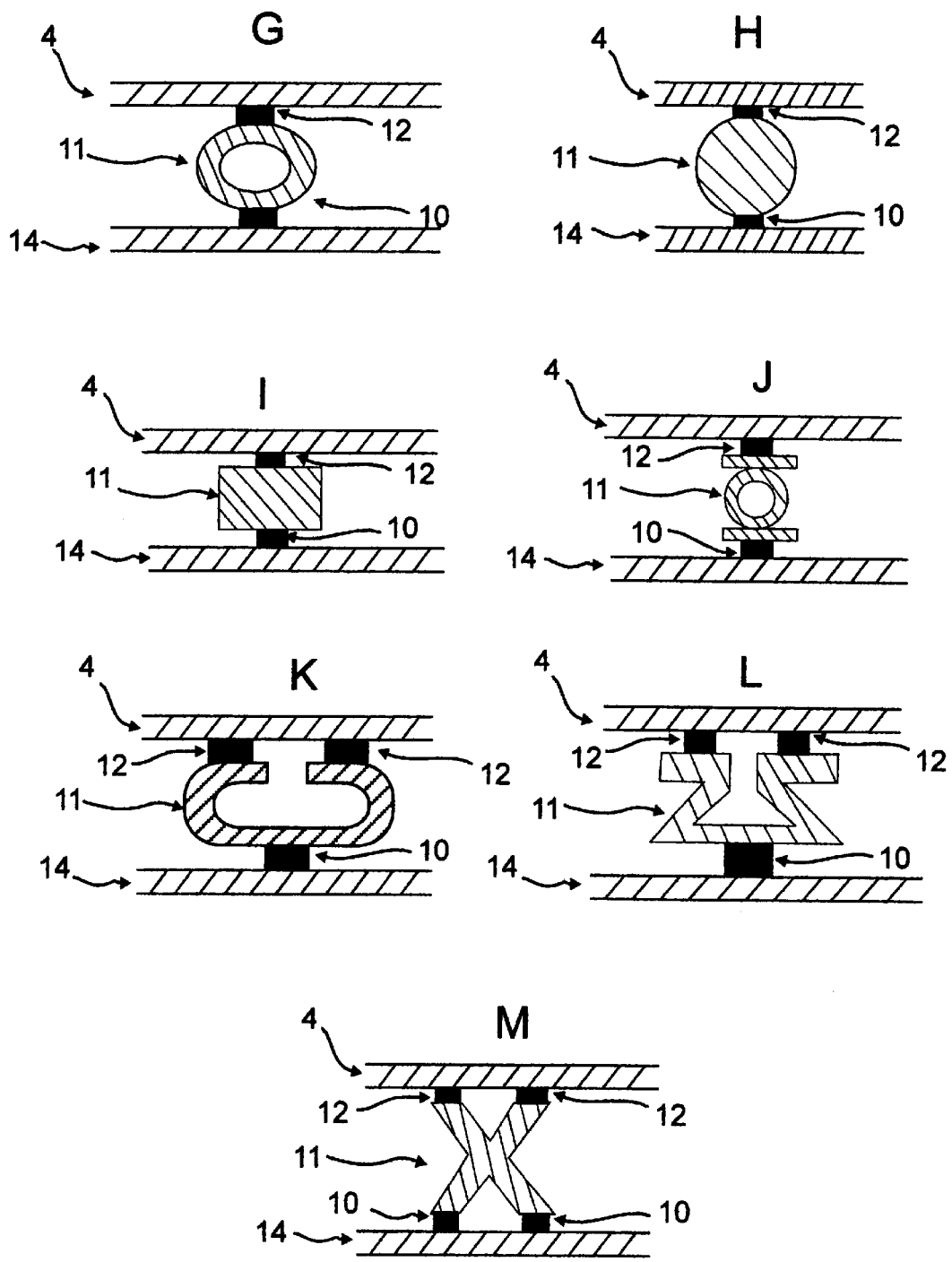
FIG. 3 shows sectioned A to M variants of suitable configurations of the independent tension relief structure.

As schematically indicated in the several exemplifying illustrations of FIG. 3, the structure 11 can also be obtained in a variety of shapes, but in these examples the structure 11 is attached in a non-releasable way to the lining layer 4 of the wing 5 by means of an attachment region 12, and attached in a releasable way to the undergarment 14 by means of the adhesive coated region 10 (a releasable attachment is the one that allows the separation of the adhered surface without causing any destruction or irreversible deformation thereof, while the non-releasable attachment causes such effects). Thus, it can be seen that alternative G corresponds to FIG. 1. In alternatives D, E, K, L and M, the adhesive coated region 10 and/or attachment region 12 can be configured as more than one point or line. Alternatives H and I show solid structures 11 made of elastic material, typically elastomeric material, instead of hollow structures such as D, E, G, J, K, and L.

In a particular embodiment of the invention, in accordance with the alternative of FIG. 3A, the tension relief structure 11 is in the shape of a joint wherein the arms 30 and 40 are joined by a folding line 50 parallel to the longitudinal axis of the napkin 1, the arm 30 being attached to the corresponding wing 5 by a non-releasable attachment region 12, while the other arm 40 is provided with at least one adhesive coated region 10 for attachment to the undergarment 14.

Other alternatives that are combinations of these, or also other regular and irregular shapes, are immediately perceived by one skilled in the art and included in the scope of the invention.

Said structure 11 is preferably attached to the respective wing 5 by being adhered to the non-releasable attachment region 12, but it can be attached by any other attachment means known in the art, such as ultrasonic sealing, fusion, etc. In FIG. 1, the adhered region 10 is generally made as a continuous line, but it can be made along aligned or any another equivalent way. The preferred adhesive of the region 10 is the one usually known as pressure sensitive adhesive (PSA) which is traditionally made from acrylic or rubber.

An example of the preferred embodiment having been described, it should be understood that the scope of the present invention encompasses other possible variations, being limited only by the tenor of the accompanying claims, wherein any possible equivalents are included.

What is claimed is:

1. A sanitary napkin comprising a body faceable liquid permeable top layer, a garment faceable liquid impermeable lining layer and an absorbing core intermediate the top layer and the lining layer, the sanitary napkin further including a flexible wing adapted to be folded over a crotch portion of a wearer's undergarment in use, said wing having a body faceable top layer and a garment faceable lining layer, wherein said wing is provided with a tension relief structure, the tension relief structure having a first surface affixed to the garment faceable lining layer of the wing and a second surface that is adapted to contact the undergarment in use, the second surface being movable with respect to the first surface and the second surface having an adhesive region that releasably adheres the tension relief structure to the user's undergarment.

2. A sanitary napkin according to claim 1, wherein said napkin is provided with two side wings.

3. A sanitary napkin according to claim 1, wherein the tension relief structure is attached to at least one of the wings on a side opposite to a side having the adhesive coated region.

4. A sanitary napkin according to claim 1, wherein the tension relief structure is hollow.

5. A sanitary napkin according to claim 3, wherein the tension relief structure is a cylinder positioned parallel to the longitudinal axis of the napkin.

6. A napkin according to claim 2, wherein the tension relief structure is a sphere.

7. A napkin according to claim 1, wherein the tension relief structure is in the shape of a joint formed by a first arm and a second arm, wherein the first arm is joined to the second arm by a folding line parallel to the longitudinal axis of the napkin, the first arm being attached to the corresponding wing by an attachment region, while the second arm is provided with at least one adhesive coated region for attachment to the undergarment.

8. A napkin according to claim 1, wherein the tension relief structure is made of elastic material.

9. A napkin according to claim 1, wherein the tension relief structure is made of corrugated material.

\* \* \* \* \*